United States Patent [19]

Norris

[11] 4,417,894
[45] Nov. 29, 1983

[54] TOWELSHEET DISPOSABLE DIAPER

[76] Inventor: Kenneth E. Norris, 61352 Tombstone Dr., Montrose, Colo. 81401

[21] Appl. No.: 357,303

[22] Filed: Mar. 11, 1982

[51] Int. Cl.³ .............................................. A61F 13/16
[52] U.S. Cl. ..................................... 604/385; 604/358
[58] Field of Search ............... 604/358, 364, 367, 372, 604/374, 378, 385

[56] References Cited

U.S. PATENT DOCUMENTS 2,916,037  12/1959  Hansen ................................ 604/365
3,585,998  6/1971   Hayford et al. ..................... 604/359
3,585,999  6/1971   Wanberg ............................. 604/385

Primary Examiner—C. Fred Rosenbaum
Assistant Examiner—Sherri F. Vinyard

[57] ABSTRACT

An improved disposable diaper, containing a towelsheet superposed on or above the backsheet of the diaper. When the diaper is messy the towelsheet may be unfastened at the bottom area of the diaper, and used as a towel to clean solid waste from the child during the diaper removal process.

4 Claims, 2 Drawing Figures

TOWELSHEET DISPOSABLE DIAPER

BACKGROUND OF THE INVENTION

1. Field of the Invention

The invention relates generally to an improved disposable diaper which facilitates easy cleanup of a child having a messy diaper.

2. Description of the Prior Art

A disposable diaper is used on a child for convenience, so that when wet or messy, the diaper may be discarded. The problem with disposable diapers currently in use is that when a child is messy and the diaper is removed, part of the solid waste from the child remains on the child for further cleanup. This invention minimizes this problem.

SUMMARY OF THE INVENTION

The invention relates to an improved disposable diaper which facilitates cleanup of a child with a messy diaper. The improved diaper contains a towelsheet which may be used to clean solid waste from the child during the process of messy diaper removal.

It is an object of the invention to provide a disposable diaper which is more convenient than existing disposable diapers.

DESCRIPTION OF THE PREFERRED EMBODIMENT

Figure 1:
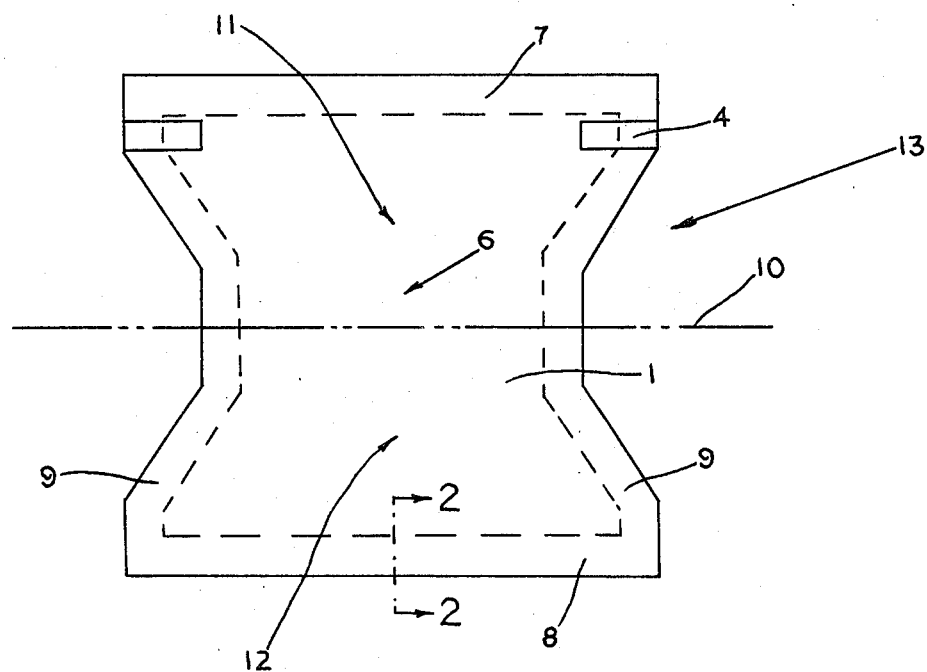
FIG. 1 is a view showing an unfolded Towelsheet Disposable Diaper.
Figure 2:
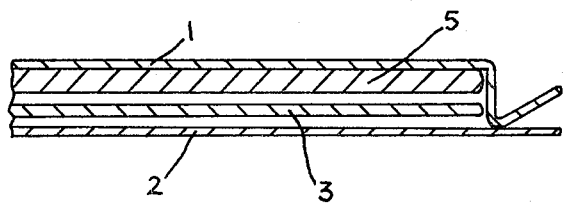
FIG. 2 is a sectional view, along Section 2—2 of FIG. 1.

Referring to FIGS. 1 and 2, an embodiment of the Towelsheet Disposable Diaper is shown.

In this embodiment, a topsheet 1 is shown which contacts the child when the diaper 13 is on the child. For the purposes of this invention the term child includes persons of all ages. The topsheet 1 passes moisture from the child through to an absorbent body 5. The backsheet 2 of the diaper 13 is moisture resistant and prevents moisture from escaping from the diaper 13 through the backsheet 2. The towelsheet 3, in this embodiment, is sandwiched between the absorbent body 5 and the backsheet 2. In other embodiments the towelsheet 3 may be superposed on the absorbent body 5. The towelsheet 3 may be made of any material suitable for wiping solid waste from the child. The towelsheet 3 may be made of moisture absorbent material, to absorb wetness from the child which would allow the absorbent body 5 to be made thinner for a like amount of moisture absorbency.

In this embodiment, the topsheet 1 and backsheet 2 are fastened at the top lateral edge 7, the side lateral edges 9 and the bottom lateral edge 8 of the diaper 13.

The towelsheet 3 is shown sandwiched between the absorbent body 5 and the backsheet 2, and is fastened to the diaper 13 at the top lateral edge 7, but is unattached at the bottom lateral edge 8 and the side lateral edges 9. However, in other embodiments the towelsheet 3 may be fastened to other parts of the diaper 13, as necessary.

The towelsheet 3 may be fastened to the diaper 13 at any location or locations within the top area 11, which in most embodiments is that part of the diaper 13 located above the lateral center line 10. In some embodiments, the top area 11 may be defined as also extending somewhat below the lateral center line 10, which will still allow the invention to function. The diaper 13 also contains a bottom area 12, which in most embodiments, is that part of the diaper 13 located below the lateral center line 10. In some embodiments the bottom area 12 may be defined to also extend above the lateral center line 10. In any event, for the invention to function, the towelsheet 3 must remain fastened to the diaper 13 at such a location or locations and in such a manner as to allow part or all of the towelsheet 3 to be freed from the diaper 13 in such a manner and at such a location as to allow the towelsheet 3 to be effectively used as a towel for cleaning solid waste from the child.

The diaper 13 also contains a crotch area 6 which is located in the area of the lateral center line 10.

When the diaper 13 is messy, the adhesive tapes 4 are torn loose from the diaper 13 and the diaper 13 is unfolded. In this embodiment, the topsheet 1 is unfastened from the diaper 13 along the bottom lateral edge 8 and side lateral edges 9, as necessary, to free the towelsheet 3. The topsheet 1 and absorbent body 5 are folded under, with the messy surfaces together, to provide a clean surface for the child to rest on. Then the towelsheet 3 is used to wipe the remaining solid waste from the child. A multiplicity of towelsheets 3 can be used to clean more effectively. By the use of the towelsheet 3, the inconvenience of additional cleaning of the child is minimized.

Although one detailed embodiment of the invention is illustrated in the drawings and previously described in detail, this invention contemplates any configuration, design and relationship of components which will function in a similar manner and which will provide the equivalent result.

I claim:

1. In an integral disposable diaper having a backsheet and an absorbent body superposed on and associated with the backsheet, an improvement, comprising:

a towelsheet, which is fastened to the diaper at the top area of the diaper, and which is removably fastened at the bottom area of the diaper such that when unfastened forms a towel, integral with the diaper, for cleaning a messy child, in which the towelsheet is of moisture absorbent material and is sandwiched between the backsheet and the absorbent body, with a substantial portion of the towelsheet extending over the backsheet.

2. The improvement recited in claim 1, in which the towelsheet is permanently fastened to the backsheet at the top lateral edge.

3. The improvement recited in claim 2, in which the towelsheet is removably attached to the backsheet along the bottom lateral edge.

4. The improvement recited in claim 2, in which the towelsheet is unattached to the backsheet along the bottom lateral edge.

* * * * *